United States Patent
Kase

(10) Patent No.: US 11,452,560 B2
(45) Date of Patent: Sep. 27, 2022

(54) TREATMENT TOOL WITH JAWS

(71) Applicant: Olympus Corporation, Hachioji (JP)

(72) Inventor: Seigo Kase, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 380 days.

(21) Appl. No.: 16/739,910

(22) Filed: Jan. 10, 2020

(65) Prior Publication Data

US 2020/0146748 A1 May 14, 2020

Related U.S. Application Data

(63) Continuation of application No. PCT/JP2017/025667, filed on Jul. 14, 2017.

(51) Int. Cl.
*A61B 18/14* (2006.01)
*A61B 17/29* (2006.01)

(52) U.S. Cl.
CPC .. *A61B 18/1445* (2013.01); *A61B 2017/2939* (2013.01)

(58) Field of Classification Search
None
See application file for complete search history.

(56) References Cited

U.S. PATENT DOCUMENTS

| | | | |
|---|---|---|---|
| 2004/0193212 A1* | 9/2004 | Taniguchi | A61B 17/29 606/205 |
| 2006/0217697 A1 | 9/2006 | Lau et al. | |
| 2015/0164575 A1 | 6/2015 | Lau et al. | |
| 2017/0000556 A1* | 1/2017 | Morisaki | A61B 18/1206 |
| 2018/0042638 A1 | 2/2018 | Hirai et al. | |
| 2018/0098809 A1 | 4/2018 | Miyazaki | |

FOREIGN PATENT DOCUMENTS

| | | |
|---|---|---|
| JP | 2012-250079 A | 12/2012 |
| WO | 2015137139 A1 | 9/2015 |
| WO | 2016163450 A1 | 10/2016 |
| WO | 2016208384 A1 | 12/2016 |

OTHER PUBLICATIONS

Oct. 3, 2017 International Search Report issued in International Patent Application No. PCT/JP2017/025667.
Jan. 14, 2020 Translation of International Preliminary Report on Patentability issued in International Patent Application No. PCT/JP2017/025667.

* cited by examiner

*Primary Examiner* — Joanne M Hoffman
*Assistant Examiner* — Nora W Rhodes
(74) *Attorney, Agent, or Firm* — Oliff PLC

(57) ABSTRACT

The disclosed technology is directed to a treatment tool comprises a shaft to extend from a proximal-end side toward a distal-end side. A first jaw is disposed on the distal-end portion of the shaft. A second jaw having a gripping surface that faces the first jaw, an opposed back surface of the gripping surface and a first engaging portion. The second jaw is angularly movable about a turn axis of the first engaging portion so as to be opened or closed with respect to the first jaw. A movable shaft having a recess defined in a distal-end and is movable along the longitudinal axis with respect to the shaft for angularly moving the second jaw about the turn axis with respect to the first jaw. A cover having a protrusion that protrudes toward a proximal-end side of the second jaw and a second engaging portion formed on the protrusion.

9 Claims, 10 Drawing Sheets

TREATMENT TOOL WITH JAWS

CROSS-REFERENCE TO RELATED APPLICATION

This application is a continuation application of PCT Application No. PCT/JP 2017/025667 filed on Jul. 14, 2017, which is hereby incorporated by reference in its entirety.

TECHNICAL FIELD

The disclosed technology relates to a treatment tool for treating a treatment target gripped between a pair of grip members.

DESCRIPTION OF THE RELATED ART

US Patent Application 2015/0164575A1 discloses a treatment tool for treating a treatment target such as a biotissue or the like gripped between a pair of jaws. The treatment tool includes heat generating elements disposed respectively in the jaws. Heat generated by the heat generating elements is applied to the treatment target gripped between the pair of jaws to coagulate and/or incise the treatment target.

With the treatment tool disclosed in US Patent Application 2015/0164575A1, heat insulating covers are mounted respectively on the jaws. The covers prevent heat from being transmitted to other biotissue than the treatment target. The covers are mounted on the jaws by snap fitting or the like that uses resiliency for operation. In this case, the covers need to be mounted on the jaws such that the covers will not come off the jaws even if the covers are deformed by heat produced in a treatment or the like.

The disclosed technology has been made in view of the problem described hereinbefore.

BRIEF SUMMARY OF EMBODIMENTS

The disclosed technology is directed to a treatment tool comprises an elongated shaft configured to extend from a proximal-end side toward a distal-end side along a longitudinal axis. A first jaw is disposed on the distal-end portion of the shaft. A second jaw having a gripping surface that faces the first jaw, an opposed back surface of the gripping surface and a first engaging portion. The second jaw is angularly movable about a turn axis of the first engaging portion so as to be opened or closed with respect to the first jaw. A movable shaft having a recess defined in a distal-end thereof and is movable along the longitudinal axis with respect to the shaft for angularly moving the second jaw about the turn axis with respect to the first jaw. A cover having a protrusion that protrudes toward a proximal-end side of the second jaw and a second engaging portion formed on the protrusion. The cover is disposed on the back surface of the second jaw in which the protrusion is disposed in the recess. The cover and the movable shaft being connected to one another by the second engaging portion and the second jaw and the movable shaft are connected to one another by the first engaging portion.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

DETAILED DESCRIPTION OF THE EMBODIMENTS

In the following description, various embodiments of the technology will be described. For purposes of explanation, specific configurations and details are set forth in order to provide a thorough understanding of the embodiments. However, it will also be apparent to one skilled in the art that the technology disclosed herein may be practiced without the specific details. Furthermore, well-known features may be omitted or simplified in order not to obscure the embodiment being described.

First Embodiment

Figure 1:
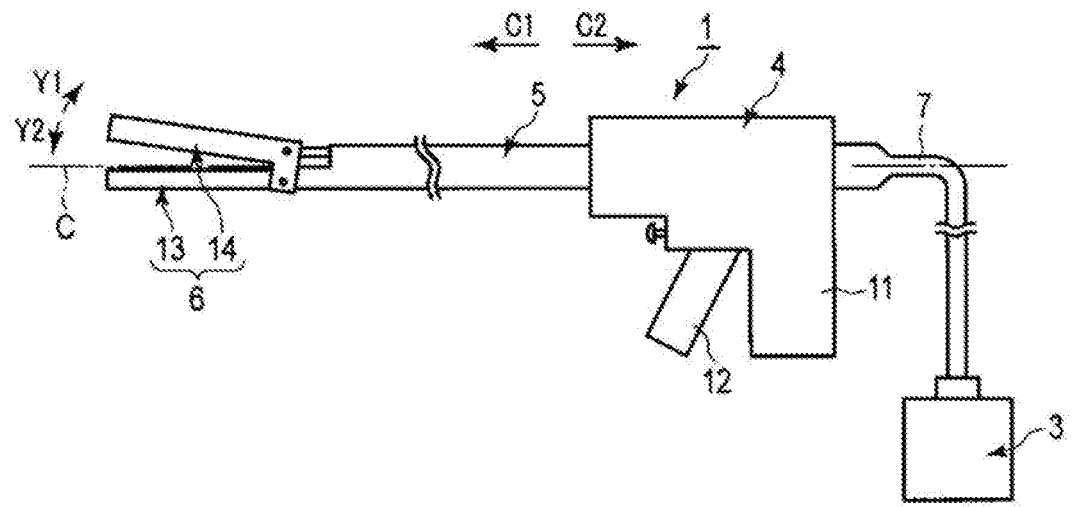
FIG. 1 is a schematic view illustrating a treatment system that uses a treatment tool according to a first embodiment.

A first embodiment of the disclosed technology will be described hereinafter with reference to FIGS. 1 through 13. FIG. 1 is a view illustrating a treatment system that uses a treatment tool 1 as a medical device according to the present embodiment. As illustrated in FIG. 1, the treatment tool 1 includes a housing 4 that can be held by hand, a shaft, i.e., outer pipe, 5 coupled to a distal-end side of the housing 4, and an end effector 6 mounted on a distal-end portion of the shaft 5. A cable 7 has an end connected to the housing 4. The other end of the cable 7 is separably connected to a power supply unit 3. The shaft 5 extends along a longitudinal axis C as a central axis thereof. One side pointed by one of the directions along the longitudinal axis C is referred to as a distal-end side indicated by an arrow C1, whereas the other side pointed by the other direction is referred to as a proximal-end side indicated by an arrow C2.

The housing 4 includes a grip, i.e., fixed handle, 11, and a handle, i.e., movable handle, 12 is angularly movably attached to the housing 4. When the handle 12 is angularly moved with respect to the housing 4, the handle 12 is opened or closed with respect to the grip 11. According to the present embodiment, the handle 12 is positioned on a distal-end side with respect to the grip 11 and moves substantially parallel to the longitudinal axis C as it is opened or closed with respect to the grip 11. However, the disclosed technology is not limited to such details. According to another embodiment, for example, the handle 12 may be positioned on a proximal-end side with respect to the grip 11. According to another embodiment, furthermore, the handle 12 may be positioned on a side of the longitudinal axis C opposite the grip 11 and may be moved in directions transverse, i.e., substantially perpendicular, to the longitudinal axis C as it is opened or closed with respect to the grip 11.

Figure 2:
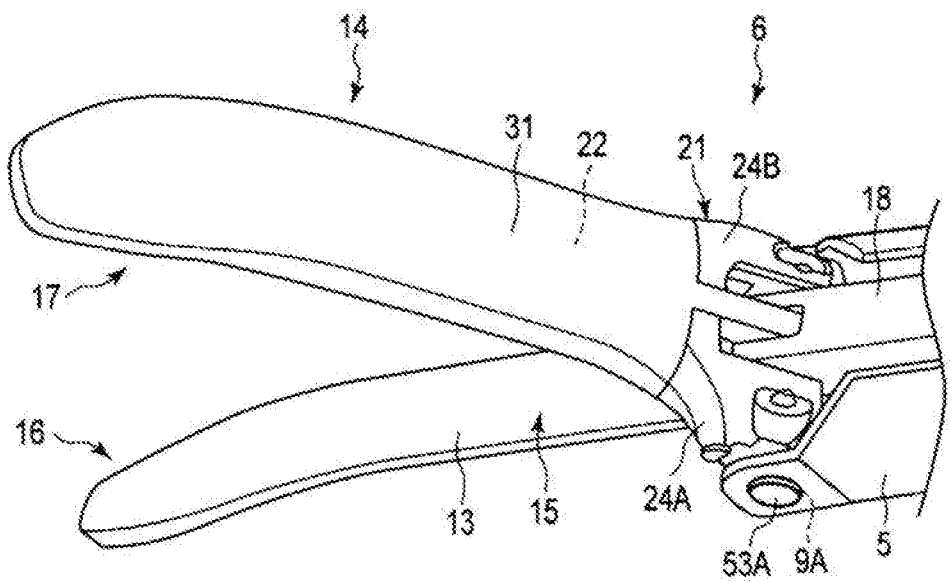
FIG. 2 is a perspective view schematically illustrating an end effector according to the first embodiment.

FIG. 2 is a view illustrating the distal-end portion of the shaft 5 and the end effector 6. As illustrated in FIG. 2, the end effector 6 includes a first grip member, i.e., first jaw, 13 and a second grip member 14 that is openable and closable with respect to the first grip member 13. The first grip member 13 has a first facing surface 16 that faces the second grip member 14. The second grip member 14 has a second facing surface, i.e., gripping surface, 17 that faces the first facing surface 16 of the first grip member 13.

The second grip member 14 is angularly movably mounted on the distal-end portion of the shaft 5 for angular movement about a turn axis. The handle 12 and the second grip member 14 are operatively coupled to each other by a movable shaft, i.e., inner pipe, 18 that extends along the longitudinal axis C in the shaft 5. When the handle 12, which functions as an opening and closing operation input part, is opened or closed with respect to the grip 11, the movable shaft 18 moves along the longitudinal axis C with respect to the shaft 5 and the housing 4, opening or closing the pair of grip members 13 and 14 with respect to each other. When the grip members 13 and 14 are closed with respect to each other, the first facing surface 16 and the second facing surface 17 grip a biotissue such as a blood vessel or the like as a treatment target therebetween.

The movable shaft 18 may extend along the longitudinal axis C outside of the shaft 5. In this case, the movable shaft 18 is in the form of a hollow tube extending along the longitudinal axis C, and the shaft 5 extends along the longitudinal axis C within the movable shaft 18.

The end effector 6 is opened and closed in directions transverse, i.e., substantially perpendicular, to the longitudinal axis C. Of the opening and closing directions of the end effector 6, the direction in which the second grip member 14 is opened away from the first grip member 13 is referred to as an opening direction, indicated by an arrow Y1 in FIG. 1, of the second grip member 14, and the direction in which the second grip member 14 is closed toward the first grip member 13 is referred to as a closing direction, indicated by an arrow Y2 in FIG. 1, of the second grip member 14. In addition, directions that are transverse, i.e., substantially perpendicular, to the longitudinal axis C and that are transverse, i.e., substantially perpendicular, to the opening and closing directions of the end effector 6 are referred to as widthwise directions.

A rod member, i.e., probe, 15 that extends along the longitudinal axis C is inserted in the shaft 5. The rod member 15 protrudes from the distal end of the shaft 5 toward the distal-end side. According to the present embodiment, the portion of the rod member 15 that protrudes from the shaft 5 toward the distal-end side is formed as the first grip member 13.

According to an embodiment, the first grip member 13 is integrally formed with the shaft 5. According to another embodiment, both the first grip member 13 and the second grip member 14 are angularly movably mounted on the distal-end portion of the shaft 5.

The rod member 15 has a proximal end connected to an ultrasonic transducer, not illustrated, disposed in the housing 4. The ultrasonic transducer is electrically connected to the power supply unit 3 by an electric path extending in the housing 4 and the cable 7. The ultrasonic transducer converts electric energy, i.e., alternating current (AC) electric power, supplied from the power supply unit 3 into ultrasonic vibrations, which are transmitted to the rod member 15. The transmitted ultrasonic vibrations are transmitted through the rod member 15 to the first grip member 13 of the end effector 6. The transmitted ultrasonic vibrations are then applied as a treatment energy to the treatment target gripped between the grip members 13 and 14.

The second grip member 14 includes a jaw, i.e., second jaw, 21. The jaw 21 is made of metal such as stainless steel or the like. Therefore, the jaw 21 is electrically conductive. The jaw 21 includes a jaw body 22. A cover, i.e., thermally insulative cover, 31 is mounted on the jaw body 22. The cover 31 forms part of an exposed surface of the second grip member 14 that is exposed outwardly. The cover 31 is made of resin such as super engineering plastics or the like, ceramics, rubber, or the like. The cover 31 is formed separately from the jaw 21. The cover 31 is electrically insulative and thermally insulative.

Figure 3:
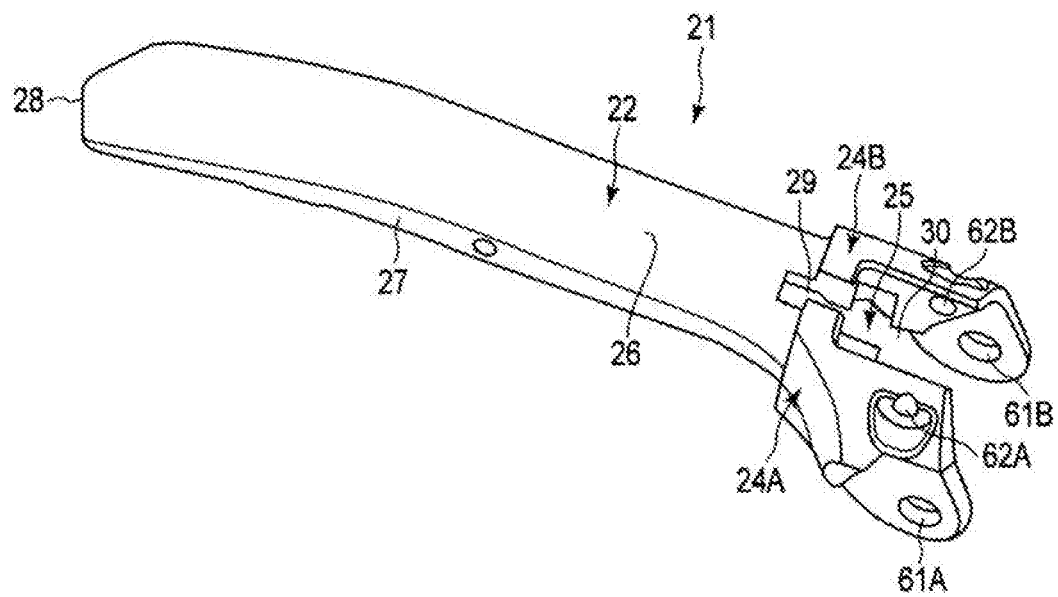
FIG. 3 is a perspective view schematically illustrating a jaw according to the first embodiment.

FIG. 3 is a view illustrating the jaw body 22 only. As illustrated in FIG. 3, the jaw body 22 includes a back surface 26 that faces a side opposite the side where the first grip member 13 is disposed, side surfaces 27 that face in the widthwise directions of the second grip member 14, and a distal-end surface 28 that faces the distal-end side.

The jaw 21 includes a pair of protrusive members, i.e., arm portions, 24A and 24B extending from the proximal-end portion of the jaw body 22 toward the proximal-end side. The protrusive members 24A and 24B are spaced apart from one another in the widthwise directions. Therefore, a groove 25 that is recessed toward the distal-end side is defined in the proximal-end portion of the jaw 21 by the protrusive members 24A and 24B and the jaw body 22. The groove 25 is defined fully across the jaw 21 in the opening and closing directions of the grip member 14.

The groove 25 includes a distal-end-side groove, i.e., recess, 29 extending in the jaw body 22 toward the proximal-end side and a proximal-end-side groove 30 positioned more toward the proximal-end side than the distal-end-side groove 29. The distance between the protrusive members 24A and 24B in the widthwise directions is smaller across the distal-end-side groove 29 than across the proximal-end-side groove 30.

The protrusive member 24A has a hole 61A defined therein. The hole 61A extends along the widthwise directions and goes through the protrusive member 24A in the widthwise directions. The protrusive member 24B has a hole 61B defined therein. The hole 61B extends along the widthwise directions and goes through the protrusive member 24B in the widthwise directions. The holes 61A and 61B are spaced from each other in the widthwise directions. The holes 61A and 61B are disposed coaxially, i.e., concentrically, with each other. The jaw 21 is angularly movably mounted on the shaft 5 by support pins 53A and 53B inserted respectively in the holes 61A and 61B.

The protrusive member 24A has a hole, i.e., first hole, 62A defined therein. The hole 62A extends along the widthwise directions and goes through the protrusive member 24A in the widthwise directions. The hole 62A is positioned farther along the opening direction of the grip member 14 than the hole 61A, i.e., on the back surface 26 side of the jaw 21. The protrusive member 24B has a hole, i.e., first hole, 62B defined therein. The hole 62B extends along the widthwise directions and goes through the protrusive member 24B in the widthwise directions. The hole 62B is positioned farther along the opening direction of the grip member 14 than the hole 61B, i.e., on the back surface 26 side of the jaw 21. The holes 62A and 62B are spaced from each other in the widthwise directions. The holes 62A and 62B are disposed coaxially, i.e., concentrically, with each other.

Figure 4:
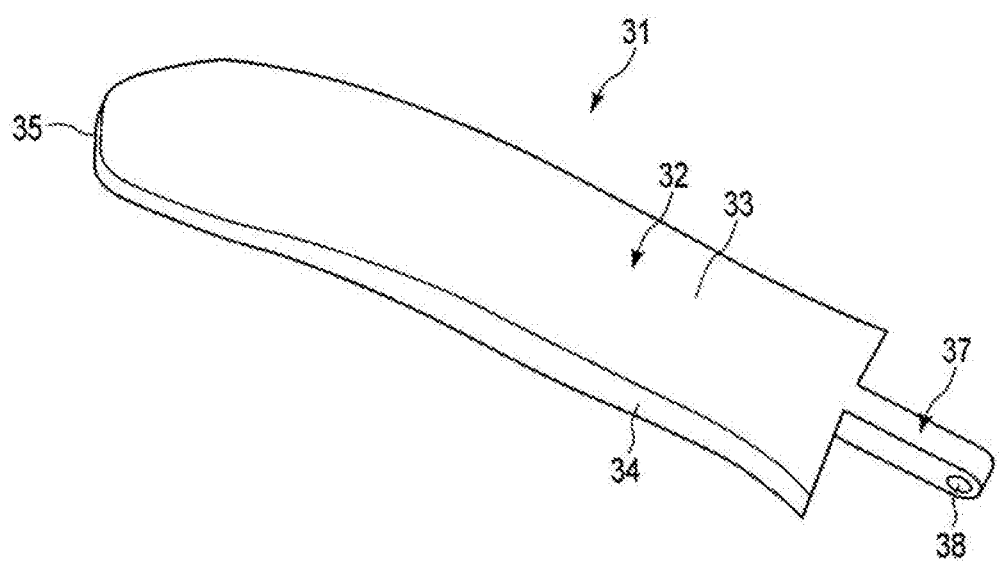
FIG. 4 is a perspective view schematically illustrating a cover according to the first embodiment.
Figure 5:
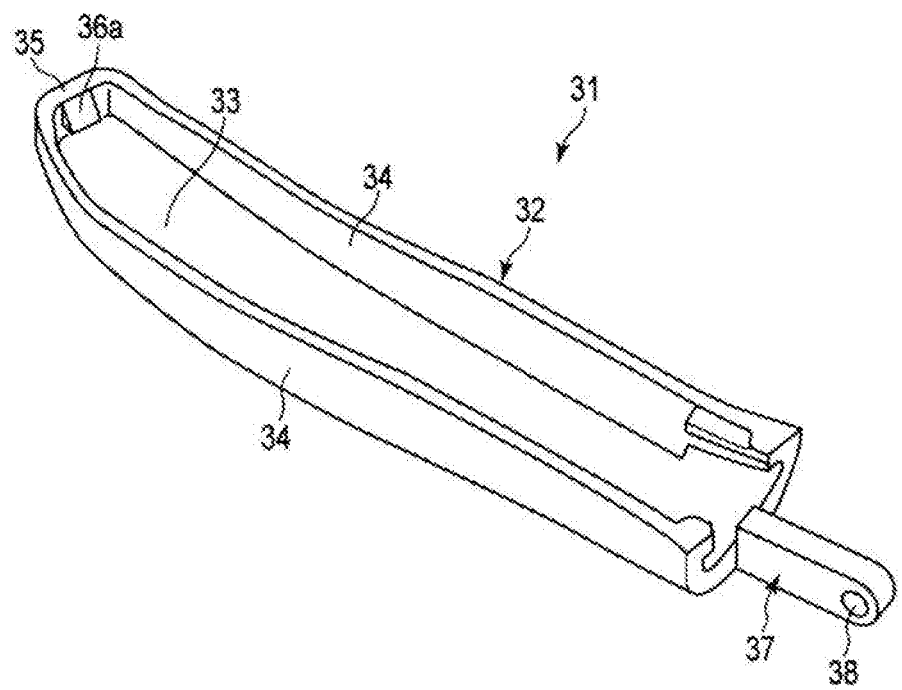
FIG. 5 is a perspective view schematically illustrating the cover according to the first embodiment as viewed from a side opposite to the side illustrated in FIG. 4.
Figure 6:
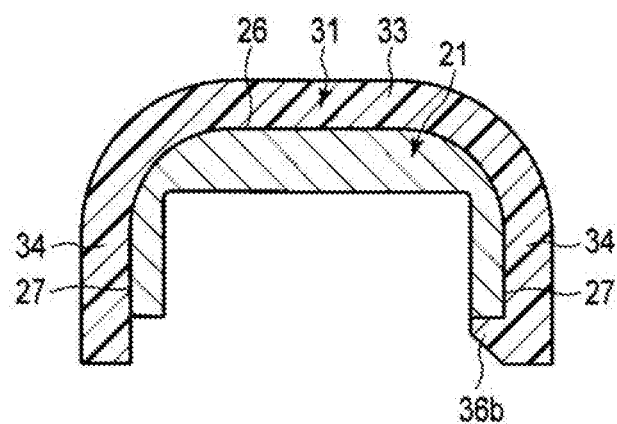
FIG. 6 is a view schematically illustrating a cross section of the jaw and the cover according to the first embodiment that extends substantially perpendicularly to the directions in which the jaw extends.
Figure 7:
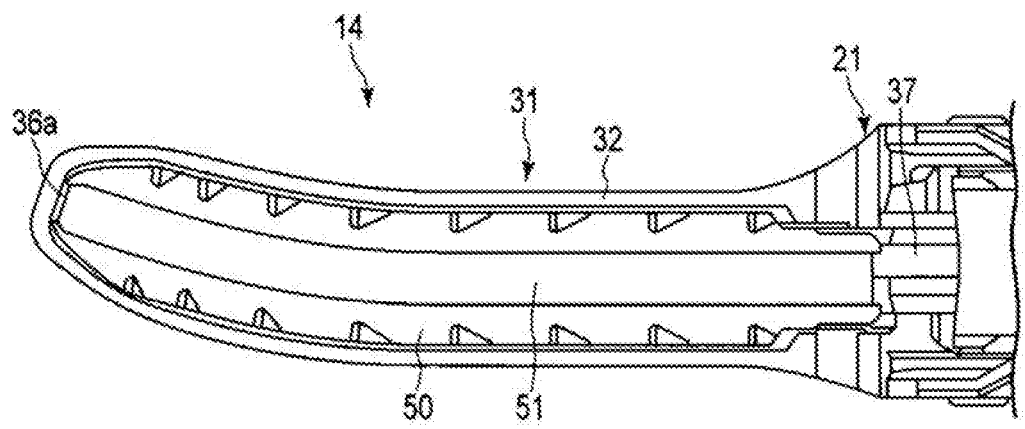
FIG. 7 is a schematic view of a second grip member according to the first embodiment as viewed from the side where a first grip member is disposed.
Figure 8:
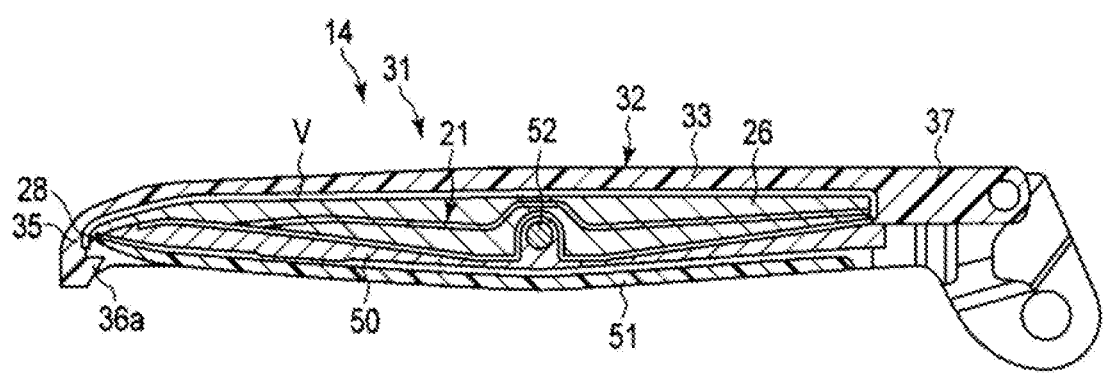
FIG. 8 is a view schematically illustrating a cross section of the second grip member according to the first embodiment that extends substantially perpendicularly to the widthwise directions of the second grip member.

FIGS. 4 and 5 are views illustrating the cover 31 only. FIGS. 6 through 8 are views illustrating the cover 31 mounted on the jaw 21. As illustrated in FIGS. 4 through 8, the cover 31 includes a cover body 32. The cover body 32 is shaped to cover an outer side of the jaw body 22. The cover body 32 includes a back surface covering portion 33 mounted on the back surface 26 of the jaw body 22, side surface covering portions 34 mounted respectively on the side surfaces 27 of the jaw body 22, and a distal-end surface covering portion 35 mounted on the distal-end surface 28 of the jaw body 22.

The cover 31 is mounted on the jaw body 22 of the jaw 21 by snap fitting or the like. According to the present embodiment, a hook 36a that projects toward the proximal-end side is disposed on an inner surface of the distal-end surface covering portion 35. A hook 36b that projects inwardly in one of the widthwise directions is disposed on an end portion of one of the side surface covering portions 34 in the closing direction of the second grip member 14. The cover 31 and the jaw 21 engage each other when the hooks 36a and 36b abut against the jaw body 22.

As illustrated in FIG. 8, when the cover 31 is mounted on the jaw 21, the jaw body 22 and the cover 31 are spaced from each other. Therefore, a gap V is created between the jaw body 22 and the cover 31.

As illustrated in FIGS. 7 and 8, the jaw 21 includes a holder member, i.e., electrode, 50 and an abutment member 51 mounted on the holder member 50. The holder member 50 is disposed along the directions in which the second grip member 14 extends, and is made of metal such as stainless steel or the like. The holder member 50 is mounted on the first grip member 13 side of the jaw body 22, and forms part of the second facing surface 17. The holder member 50 is swingably mounted on the jaw body 22 by a pin, i.e., see-saw pin, 52. The pin 52 extends along the widthwise directions of the second grip member 14.

Each of the first grip member 13 and the second grip member 14 has at least a portion made of an electrically conductive material. In the first grip member 13, the rod member 15 is made of an electrically conductive material. In the second grip member 14, the jaw 21, the pin 52, and the holder member 50 are made of an electrically conductive material. The first grip member 13 is electrically connected to the power supply unit 3 by an electric path in the form electric wires or the like in the rod member 15 and the cable 7. The holder member 50 of the second grip member 14 is electrically connected to the power supply unit 3 by an electric path in the form electric wires or the like in the movable shaft 18 and the cable 7, and the jaw 21. When an operation input is entered by an operation button or the like while the treatment target is being gripped between the first grip member 13 and the second grip member 14, the power supply unit 3 supplies electric energy, i.e., high-frequency electric power, to the first grip member 13 and the holder member 50. When the first grip member 13 and the holder member 50 are supplied with the electric energy, i.e., high-frequency electric power, a high-frequency electric current flows between the first grip member 13 and the second grip member 14 through the gripped treatment target. At this time, the first grip member 13 and the holder member 50 act as electrodes, respectively. In this manner, the high-frequency electric current is applied as a treatment energy to the gripped treatment target.

The abutment member 51 is mounted on the holder member 50 at a side of the second grip member 14 that faces in the closing direction thereof. The abutment member 51 is disposed along the directions in which the second grip member 14 extends. The abutment member 51 of the jaw 21 forms part of the second facing surface 17. The abutment member 51 is made of an electrically nonconductive material. When the first grip member 13 and the second grip member 14 are closed with respect to each other with no treatment target disposed between the first grip member 13 and the second grip member 14, the abutment member 51 is brought into abutment against the first grip member 13, i.e., the first facing surface 16. Thus, when the first grip member 13 and the second grip member 14 are closed with respect to each other with no treatment target disposed between the first grip member 13 and the second grip member 14, a short circuit is prevented from occurring which would otherwise be caused if the respective electrodes on the first grip member 13 and the second grip member 14 contacted each other.

According to an embodiment, the jaw 21 is free of the holder member 50 and the abutment member 51, and the jaw body 22 functions as an electrode. In addition, an abutment member that is electrically insulative is disposed on the first facing surface 16 of the first grip member 13. In this case, the second facing surface, i.e., gripping surface, 17 is formed by the jaw body 22.

Figure 9:
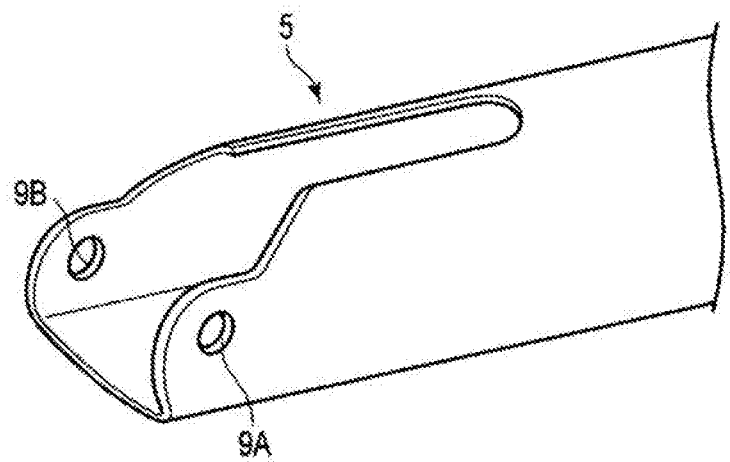
FIG. 9 is a perspective view schematically illustrating a distal-end portion of a shaft, i.e., outer pipe, according to the first embodiment.

As illustrated in FIG. 9, holes, i.e., third holes, 9A and 9B are defined in the distal-end portion of the shaft 5. Each of the holes 9A and 9B extends in the widthwise directions, and provides fluid communication between the inside and outside of the shaft 5. The holes 9A and 9B are spaced from each other in the widthwise directions. The holes 9A and 9B are disposed coaxially, i.e., concentrically, with each other.

The pin, i.e., support pin, 53A is inserted in the hole 61A and the hole 9A (see FIG. 2). Furthermore, although not illustrated in the present embodiment, the pin, i.e., support pin, 53B, is inserted in the hole 61B and the hole 9B. The pins, i.e., pins, 53A and 53B extend in the widthwise directions and are disposed coaxially with each other. The jaw 21 is angularly movable with respect to the shaft 5 about central axes of the pins 53A and 53B as a turn axis.

As illustrated in FIGS. 4 and 5, the cover 31 includes a protrusion 37 protruding from a proximal-end portion of the cover body 32 toward the proximal-end side. The protrusion 37 has a hole, i.e., second hole, 38 defined in a proximal-end portion thereof. The hole 38 extends along the widthwise directions and goes through the protrusion 37 in the widthwise directions. The hole 38 is larger than each of the holes 62A and 62B in the jaw 21. Specifically, the inside diameter of the hole 38 is larger than the inside diameter of each of the holes 62A and 62B in the jaw 21. Therefore, the hole 38 has a larger cross-sectional area along a cross section that is transverse, i.e., substantially perpendicular, to the directions in which the hole 38 extends, i.e., the axial directions thereof, than the holes 62A and 62B in the jaw 21.

Figure 10:
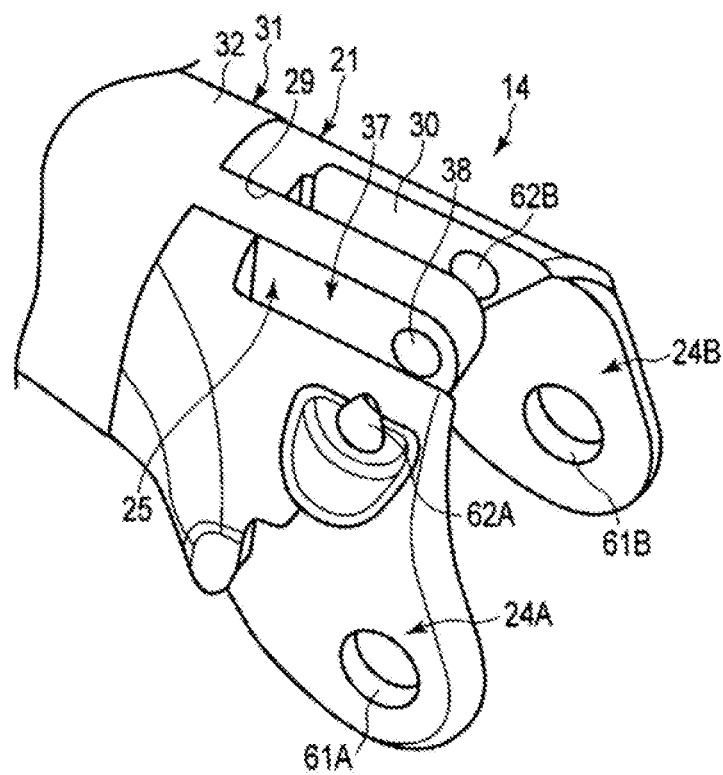
FIG. 10 is a perspective view schematically illustrating a proximal-end portion of the jaw and a proximal-end portion of the cover according to the first embodiment.

As illustrated in FIG. 10, with the cover 31 mounted on the jaw 21, the protrusion 37 of the cover 31 fits in the distal-end-side groove 29 of the groove 25 in the jaw 21 and is disposed between the protrusive members 24A and 24B in the proximal-end-side groove 30. By fitting in the distal-end-side groove 29, the protrusion 37 is fixed to the proximal-end side of the second facing surface 17 and protrudes from the proximal end of the second facing surface 17 toward the proximal-end side. The protrusion 37 and the protrusive members 24A and 24B are spaced from each other in the widthwise directions. The hole 38 in the protrusion 37 is disposed coaxially, i.e., concentrically, with the holes 62A and 62B in the jaw 21.

Figure 11:
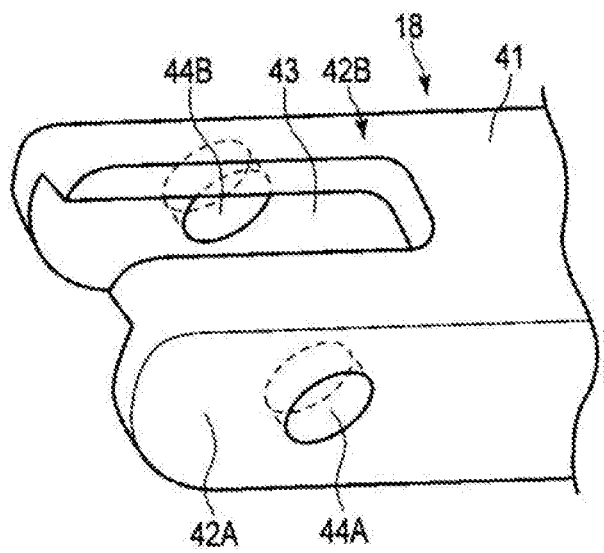
FIG. 11 is a perspective view schematically illustrating a distal-end portion of a movable shaft according to the first embodiment.

As illustrated in FIG. 11, the movable shaft 18 includes a base portion 41 extending along the longitudinal axis C and extensions 42A and 42B extending from a distal-end portion of the base portion 41 toward the distal-end side. The extensions 42A and 42B are spaced from each other in the widthwise directions. Therefore, a groove 43 that is recessed toward the proximal-end side is defined in the distal-end portion of the movable shaft 18 by the extensions 42A and 42B and the base portion 41. The groove 43 is defined fully across the movable shaft 18 in the opening and closing directions of the end effector 6, i.e., the grip members 13 and 14.

The extension 42A has a hole 44A defined therein. The hole 44A extends along the widthwise directions and goes through the extension 42A in the widthwise directions. The extension 42B has a hole 44B defined therein. The hole 44B extends along the widthwise directions and goes through the extension 42B in the widthwise directions. The holes 44A and 44B are spaced from each other in the widthwise directions. The holes 44A and 44B are disposed coaxially, i.e., concentrically, with each other.

Figure 12:
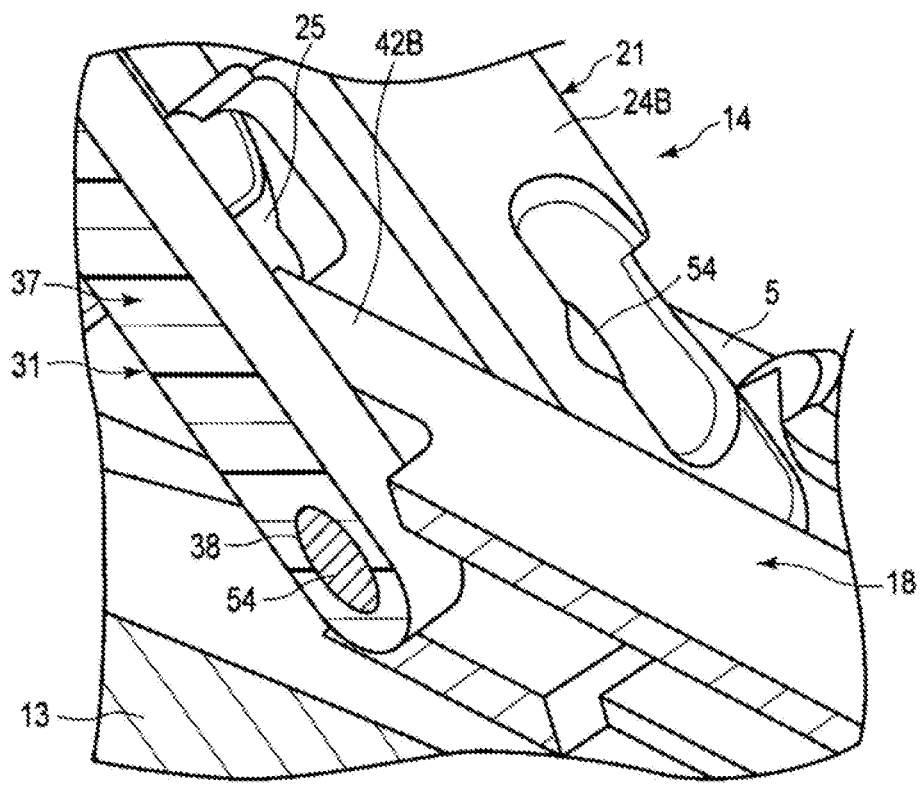
FIG. 12 is a schematic view, partly in cross section, illustrating a joint structure between the second grip member and the movable shaft according to the first embodiment.
Figure 13:
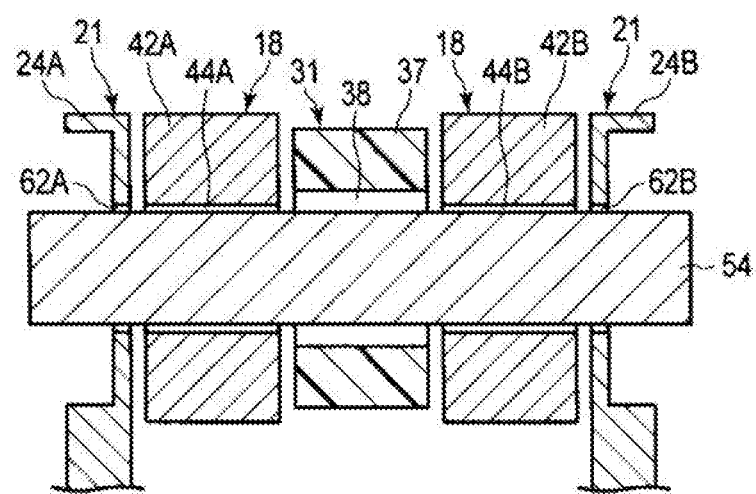
FIG. 13 is a schematic view illustrating a cross section of a joint structure between the jaw and the movable shaft according to the first embodiment that extends substantially perpendicularly to the longitudinal axis of the joint structure.

FIGS. 12 and 13 are views illustrating a joint structure between the movable shaft 18, the jaw 21, and the cover 31. As illustrated in FIGS. 12 and 13, the extensions 42A and 42B of the movable shaft 18 are disposed in the groove 25 in the jaw 21. The protrusion 37 of the cover 31 is disposed in the groove 43 in the movable shaft 18. Therefore, the protrusive member 24A of the jaw 21 is disposed outside of the extension 42A of the movable shaft 18 in the widthwise directions, and the protrusion 37 is disposed between, i.e., inside of, the extensions 42A and 42B in the widthwise directions. Furthermore, the protrusive member 24B of the jaw 21 is disposed outside of the extension 42B of the movable shaft 18 in the widthwise directions, and the protrusion 37 is disposed between, i.e., inside of, the extensions 42A and 42B in the widthwise directions. The holes 62A and 62B in the protrusive members 24A and 24B, the holes 44A and 44B in the extensions 42A and 42B, and the hole 38 in the protrusion 37 are disposed coaxially, i.e., concentrically, with each other. A pin, i.e., jaw rear pin, 54 is inserted in the holes 62A and 62B, the holes 44A and 44B, and the hole 38. The pin 54 extends in the widthwise directions, and go through the holes 62A and 62B, the holes 44A and 44B, and the hole 38. Consequently, the pin 54 has a central axis, i.e., axial directions, substantially parallel to the widthwise directions. The pin 54 is fixed to the jaw 21 in the holes 62A and 62B by welding or the like.

The jaw 21 is mounted on the movable shaft 18 by the pin 54 inserted in the holes 62A and 62B and the holes 44A and 44B. The pin 54 is movable in the holes 44A and 44B with respect to the movable shaft 18. When the pin 54 is moved with respect to the movable shaft 18, the holes 62A and 62B in the jaw 21 fixed to the pin 54 are moved in unison with the pin 54 with respect to the movable shaft 18.

For example, with the grip members 13 and 14 being open away from each other, when the handle 12 is operated to move the movable shaft 18 toward the distal-end side with respect to the shaft 5, the pin 54 is pressed toward the distal-end side from inner circumferential surfaces of the holes 44A and 44B. As the pin 54 is pressed toward the distal-end side, the pin 54 is moved in unison with the movable shaft 18 with respect to the shaft 5 toward the distal-end side. At this time, the pin 54 presses edges of the holes 62A and 62B in the jaw 21 within the holes 62A and 62B toward the distal-end side. When the edges of the holes 62A and 62B are pressed toward the distal-end side by the pin 54, the holes 62A and 62B are moved in unison with the pin 54 with respect to the shaft 5 toward the distal-end side, and the jaw 21 is turned about the turn axis with respect to the shaft 5. The second grip member 14 is thus closed toward the first grip member 13. In other words, a drive force tending to move the movable shaft 18 is transmitted through the pin 54 and the edges of the holes 62A and 62B to the jaw 21, closing the second grip member 14 toward the first grip member 13.

Moreover, with the grip members 13 and 14 being closed toward each other, when the handle 12 is operated to move the movable shaft 18 toward the proximal-end side with respect to the shaft 5, the pin 54 is pressed toward the proximal-end side from inner circumferential surfaces of the holes 44A and 44B. As the pin 54 is pressed toward the proximal-end side, the pin 54 is moved in unison with the movable shaft 18 with respect to the shaft 5 toward the proximal-end side. At this time, the pin 54 presses edges of the holes 62A and 62B in the jaw 21 within the holes 62A and 62B toward the proximal-end side. When the edges of the holes 62A and 62B are pressed toward the proximal-end side by the pin 54, the holes 62A and 62B are moved in unison with the pin 54 with respect to the shaft 5 toward the proximal-end side, and the jaw 21 is turned about the turn axis with respect to the shaft 5. The second grip member 14 is thus opened away from the first grip member 13. In other words, a drive force tending to move the movable shaft 18 is transmitted through the pin 54 and the edges of the holes 62A and 62B to the jaw 21, opening the second grip member 14 away from the first grip member 13.

As described hereinbefore, the inside diameter, i.e., size, of the hole 38 is larger than the inside diameters, i.e., sizes, of the holes 62A and 62B. Therefore, the inside diameter of the hole 38 is larger than the outside diameter of the pin 54 that is fixed to the jaw 21 within the holes 62A and 62B. Furthermore, the hole 38 is disposed coaxially with the pin 54. Therefore, the outer circumferential surface of the pin 54 and the edge, i.e., inner circumferential surface, of the hole 38, are spaced from each other.

Next, operation and advantages of the treatment tool 1 will be described hereinafter. For performing a treatment using the treatment tool 1, the end effector 6 is inserted into a body cavity such as an abdominal cavity or the like. Then, a treatment target is positioned between the pair of grip members 13 and 14, and an operation input is entered through the handle 12 to close the end effector 6. The treatment target is now gripped between the grip members 13 and 14. Then, an operation input is entered to supply electric energy from the power supply unit 3 to the treatment tool 1, so that at least one of ultrasonic vibrations and a high-frequency electric current, referred to hereinbefore, is applied as a treatment energy to the gripped treatment target.

According to the present embodiment, the cover 31 and the jaw 21 are formed separately from each other. In this case, the gap V is created between the jaw 21 and the cover 31. With an air layer formed in the gap V between the jaw 21 and the cover 31, the transfer of heat from the jaw 21 to the cover 31 is reduced, increasing the thermal insulation capability of the cover 31. On the other hand, there is a possibility that the cover 31 may come off the jaw 21 as the hooks 36a and 36b, etc. of the cover 31 may be elastically deformed due to the heat produced in a treatment, etc.

According to the present embodiment, the cover 31 and the pin 54 are kept in engagement with each other by the pin 54 inserted in the hole 38 defined in the protrusion 37. Therefore, even if the cover 31 is deformed, allowing the jaw 21 to disengage from the hooks 36a and 36b, etc., the cover 31 and the pin 54 are kept in engagement with each other, i.e., they are not released from engagement with each other, unless the protrusion 37 of the cover 31 is broken. Furthermore, the cover 31 is connected to the jaw 21 by the pin 54. Therefore, insofar as the engagement between the cover 31 and the pin 54 is effectively maintained, the cover 31 remains connected to the jaw 21. The cover 31 is thus prevented from coming off the jaw 21, assuring stability during a treatment.

Moreover, the jaw 21 and the movable shaft 18 are held in engagement with each other by the pin 54 inserted in the holes 44A and 44B in the movable shaft 18. Therefore, the pin 54 keeps the jaw 21 and the movable shaft 18 in engagement with each other and also keeps the cover 31 and the jaw 21 in engagement with each other. In other words, the pin 54 that keeps the movable shaft 18 and the jaw 21 in engagement with each other is used in common as an engaging member that keeps the cover 31 and the jaw 21 in engagement with each other. According to the present embodiment, therefore, as one engaging member, i.e., the pin 54, is used to keep the movable shaft 18 and the jaw 21 in engagement with each other and also to keep the cover 31 and the jaw 21 in engagement with each other, a structure for maintaining the cover 31 and the jaw 21 in engagement with each other even if the cover 31 is deformed is realized without the need for an increase the number of parts used.

Furthermore, as described hereinbefore, since the inside diameter of the hole 38 in the protrusion 37 of the cover 31 is larger than the inside diameters of the holes 62A and 62B in the jaw 21, the pin 54 is kept out of abutment against the edge of the hole 38. The cover 31 is mounted on the jaw 21 by the pin 54 and turns in unison with the jaw 21 when the jaw 21 is turned with respect to the sheath 5. Moreover, as described hereinbefore, the inside diameter of the hole 38 in the protrusion 37 of the cover 31 is larger than the inside diameters of the holes 62A and 62B in the jaw 21. Consequently, even if the pin 54 is moved with respect to the movable shaft 18 when the jaw 21 is turned with respect to the shaft 5, the pin 54 does not abut against the edge of the hole 38 in the cover 31. Since the pin 54 is prevented from contacting the edge of the hole 38 in the cover 31, the durability of the hole 38 in the cover 31 is increased, making it more effective to prevent the cover 31 from coming off the jaw 21.

The shape of the hole 38 in the cover 31 is not limited to a substantially circular shape, but may be a substantially elliptical shape, a substantially polygonal shape, or the like.

According to an embodiment, heat generated by a heater disposed in at least one of the grip members 13 and 14 is used as a treatment energy. The treatment tool 1 applies at least one of the ultraviolet vibrations, the high-frequency electric current, and the heat referred to hereinbefore as a treatment energy from the end effector 6 to the treatment target.

Figure 14:
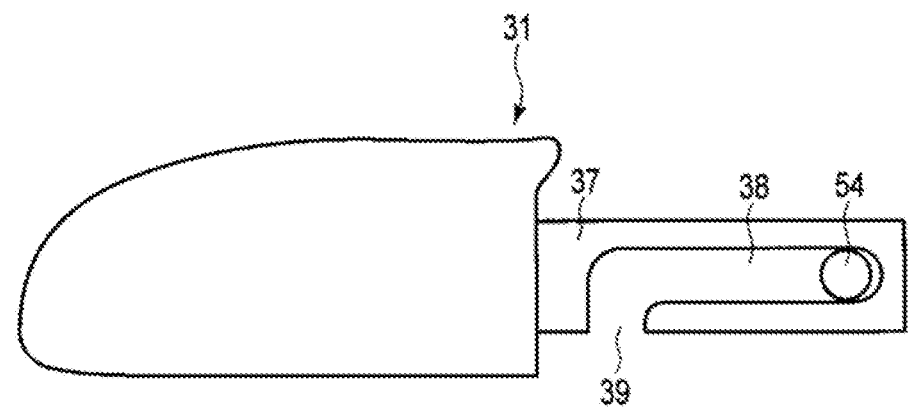
FIG. 14 is a view schematically illustrating a cover according to a first modification of the first embodiment.

According to a first modification illustrated in FIG. 14, a hole 38 has an opening 39 that is open in the closing direction of the second grip member 14. According to the present modification, when the pin 54 is to be inserted into the hole 38, the pin 54 can be inserted through the opening 39 into the hole 38. As a result, the assemblability is increased.

Figure 15:
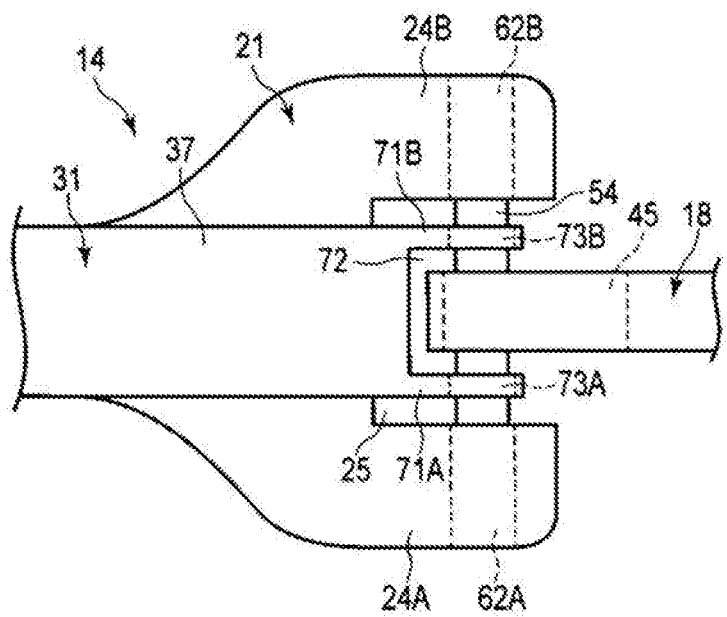
FIG. 15 is a view schematically illustrating a joint structure between a second grip member and a movable shaft according to a second modification of the first embodiment.
Figure 16:
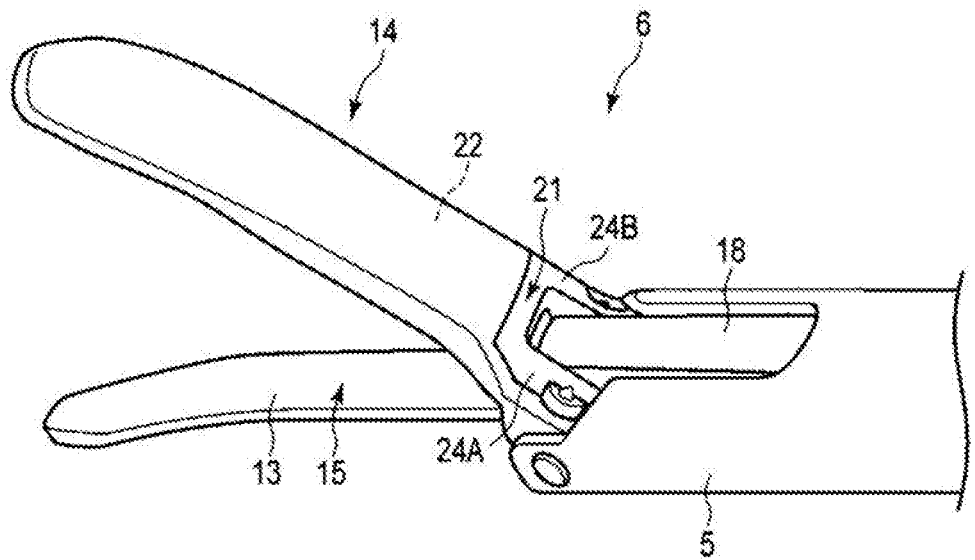
FIG. 16 is a perspective view schematically illustrating an end effector according to a second embodiment.
Figure 17:
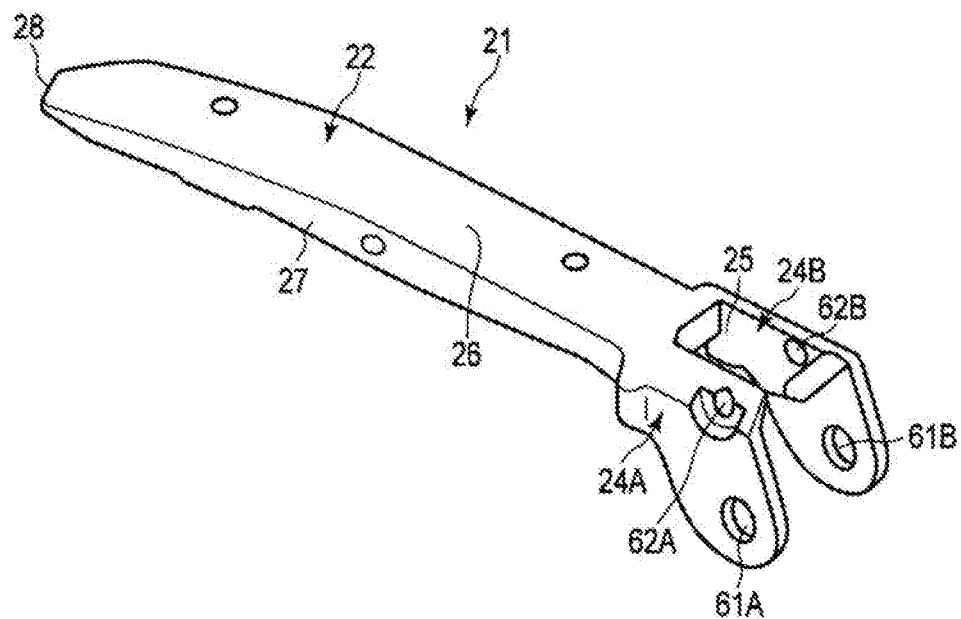
FIG. 17 is a perspective view schematically illustrating a jaw according to the second embodiment.

FIG. 15 is a view illustrating a joint structure between the second grip member 14 and the movable shaft 18 according to a second modification of the present embodiment. According to the present modification, the movable shaft 18 is free of extensions, i.e., the extensions 42A and 42B, and a groove, i.e., the groove 43. The distal-end portion of the movable shaft 18 has a hole 45 defined therein that goes through the movable shaft 18 in the widthwise directions.

The cover 31 has a protrusion 37 including protrusive members 71A and 71B. The protrusive members 71A and 71B extend from the proximal-end portion of the protrusion 37 toward the proximal-end side. The protrusive members 71A and 71B are spaced from each other in the widthwise directions. Therefore, a groove 72 that is recessed toward the distal-end side is defined in the proximal-end portion of the protrusion 37 between the protrusive member 71A and the protrusive member 71B. The groove 72 is defined fully across the end effector 6, i.e., the grip members 13 and 14, in the opening and closing directions thereof. With the cover 31 mounted on the jaw 21, the protrusive members 71A and 71B are disposed in the groove 25 in the jaw 21.

The protrusive member 71A has a hole, i.e., second hole, 73A defined therein. The hole 73A extends along the widthwise directions and goes through the protrusive member 71A in the widthwise directions. The protrusive member 71B has a hole, i.e., second hole, 73B defined therein. The hole 73B extends along the widthwise directions and goes through the protrusive member 71B in the widthwise directions. The holes 73A and 73B are spaced from each other in the widthwise directions. The holes 73A and 73B are disposed coaxially, i.e., concentrically, with each other.

The movable shaft 18 has a distal-end portion disposed in the groove 72 in the protrusion 37 of the cover 31 within the groove 25 in the jaw 21. At this time, the protrusive members 71A and 71B are disposed in sandwiching relation to the movable shaft 18 in the widthwise directions. The hole 45 in the movable shaft 18, the holes 62A and 62B in the protrusive members 24A and 24B, and the holes 73A and 73B in the protrusive members 71A and 71B are disposed coaxially with each other. The pin 54 is inserted in the hole 45, the holes 62A and 62B, and the holes 73A and 73B. The pin 54 extends along the widthwise directions and passes through the hole 45, the holes 62A and 62B, and the holes 73A and 73B.

According to the present modification, the cover 31 is connected to the jaw 21 by the pin 54 that is inserted in the holes 73A and 73B in the cover 31. The cover 31 is thus prevented from coming off the jaw 21, as described hereinbefore.

According to present embodiment, the pin 54 is fixed to the jaw 21 in the holes 62A and 62B. However, the disclosed technology is not limited to such details. According to an embodiment, the pin 54 is not fixed to the jaw 21, but is fixed to the movable shaft 18 in the holes 44A and 44B. In this case, the pin 54 is movable in the holes 44A and 44B with respect to the jaw 21. When the movable shaft 18 is moved with respect to the shaft 5, the pin 54 is moved in unison with the movable shaft 18 with respect to the shaft 5. When the pin 54 presses the edges of the holes 62A and 62B, the holes 62A and 62B are moved in unison with the pin 54 with respect to the shaft 5, and the jaw 21 is opened or closed with respect to the first grip member 13.

The hole 38 in the cover 31 is disposed coaxially with the holes 62A and 62B in the jaw 21. The inside diameter of the hole 38 is larger than the inside diameters of the holes 62A and 62B. Therefore, when the pin 54 is moved in the holes 62A and 62B and the hole 38, the pin 54 abuts against the edges of the holes 62A and 62B earlier than the edge of the hole 38. Consequently, when the pin 54 is moved in the holes 62A and 62B, the pin 54 is prevented from abutting against the edge of the hole 38 by abutting against the edges of the holes 62A and 62B prior to the edge of the hole 38. In a case where the pin 54 is fixed to the movable shaft 18, therefore, the pin 54 is prevented from abutting against the cover 31, and the durability of the cover 31 is increased as with the first embodiment.

Second Embodiment

A second embodiment of the present embodiment will be described hereinafter with reference to FIGS. 16 through 20. The second embodiment represents a modification of the first embodiment that is modified as follows. Those parts of the second embodiment that are identical to those of the first embodiment are denoted by identical numeral references, and the description of those parts will be omitted hereinafter.

Figure 18:
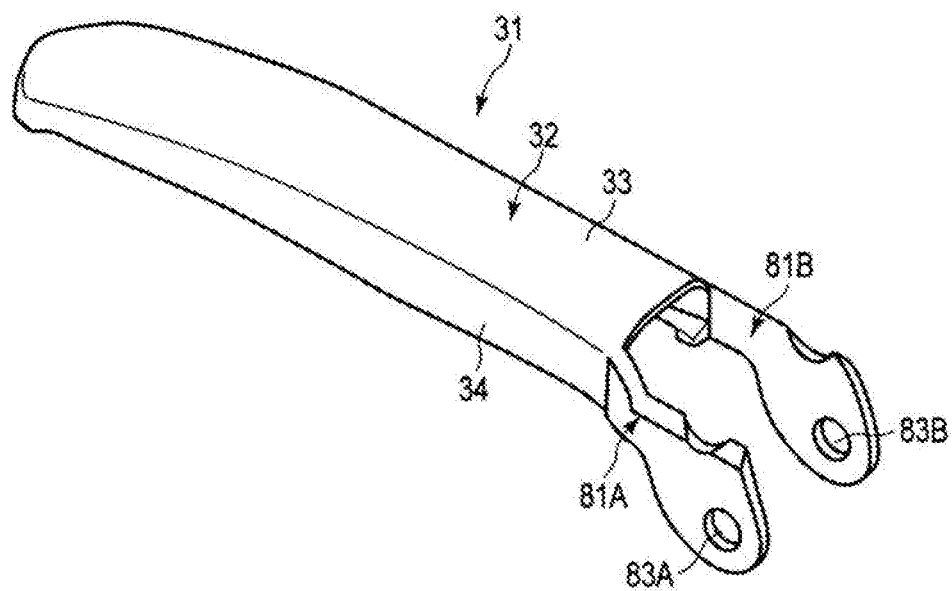
FIG. 18 is a perspective view schematically illustrating a cover according to the second embodiment.

According to the present embodiment, as illustrated in FIG. 18, the cover 31 includes extensions, i.e., protrusions, 81A and 81B. The extensions 81A and 81B extend from the proximal-end portion of the cover body 32 toward the proximal-end side. The extensions 81A and 81B are spaced from each other in the widthwise directions.

The extension 81A has a hole, i.e., second hole, 83A defined therein. The hole 83A extends along the widthwise directions and goes through the extension 81A in the widthwise directions. The extension 81B has a hole, i.e., second hole, 83B defined therein. The hole 83B extends along the widthwise directions and goes through the extension 81B in the widthwise directions. The holes 83A and 83B are spaced from each other in the widthwise directions. The holes 83A and 83B are disposed coaxially, i.e., concentrically, with each other. The inside diameters of the holes 83A and 83B are larger than the respective inside diameters of the holes 61A and 61B in the jaw 21. Therefore, the holes 83A and 83B have larger cross-sectional areas along a cross section that is transverse, i.e., substantially perpendicular, to the directions in which the holes 83A and 83B extend, i.e., the axial directions thereof, than the holes 61A and 61B.

Figure 19:
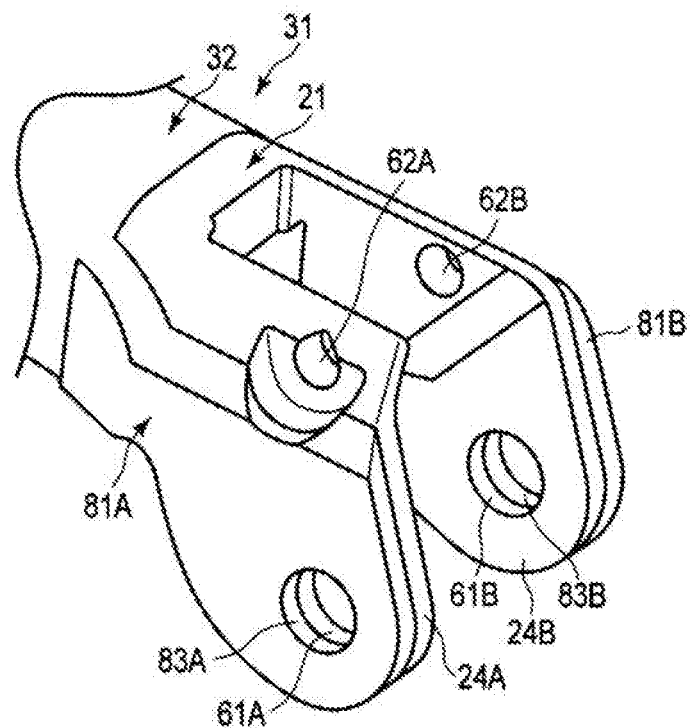
FIG. 19 is a perspective view schematically illustrating a proximal-end portion of the jaw and a proximal-end portion of the cover according to the second embodiment.

As illustrated in FIG. 19, with the cover 31 mounted on the jaw 21, the extension 81A is disposed outside of the protrusive member 24A of the jaw 21. The extension 81A is disposed over an area of the protrusive member 24A that includes the hole 61A. The hole 83A is disposed substantially coaxially with the hole 61A. The extension 81B is disposed outside of the protrusive member 24B of the jaw 21. The extension 81B is disposed over an area of the protrusive member 24B that includes the hole 61B. The hole 83B is disposed substantially coaxially with the hole 61B.

Figure 20:
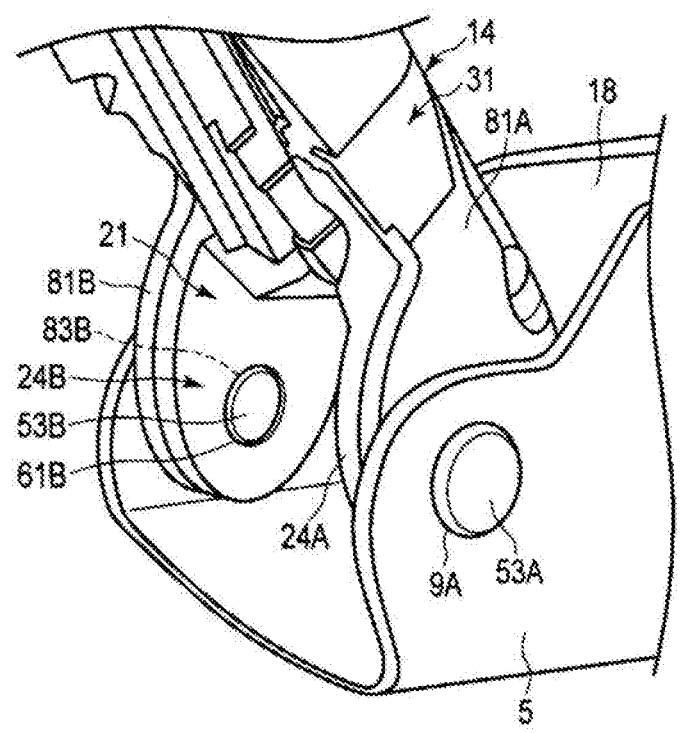
FIG. 20 is a perspective view schematically illustrating a joint structure between a second grip member and a shaft according to the second embodiment.

FIG. 20 is a view illustrating a joint structure between the jaw 21 and the shaft 5. As illustrated in FIG. 20, the protrusive members 24A and 24B of the jaw 21 are disposed inside of the shaft 5 in the widthwise directions. The hole 9A in the shaft 5 and the hole 61A in the protrusive member 24A are disposed coaxially, i.e., concentrically, with each other. The extension 81A of the cover 31 is disposed outside of the protrusive member 24A. The extension 81A is disposed between the protrusive member 24A and the shaft 5. The hole 83A is disposed coaxially with the hole 61A and the hole 9A. The pin, i.e., support pin, 53A is inserted in the hole 61A, the hole 83A, and the hole 9A. The pin, i.e., axis pin, 53A extends in the widthwise directions and goes through the hole 61A, the hole 83A, and the hole 9A. Therefore, the pin 53A has a central axis, i.e., axial directions, substantially parallel to the widthwise directions.

The hole 9B in the shaft 5 and the hole 61B in the protrusive member 24B are disposed coaxially, i.e., concentrically, with each other. The extension 81B of the cover 31 is disposed outside of the protrusive member 24B. The extension 81B is disposed between the protrusive member 24B and the shaft 5. The hole 83B is disposed coaxially with the hole 61B and the hole 9B. The pin, i.e., support pin, 53B is inserted in the hole 61B, the hole 83B, and the hole 9B. The pin, i.e., axis pin, 53B extends in the widthwise directions and goes through the hole 61B, the hole 83B, and the hole 9B. Therefore, the pin 53B has a central axis, i.e., axial directions, substantially parallel to the widthwise directions. The pins 53A and 53B are disposed coaxially with each other. The pins 53A and 53B are fixed to the jaw 21 in the holes 61A and 61B by welding or the like.

The jaw 21 is angularly movably mounted on the shaft 5 for angular movement about the central axes of the pins 53A and 53B by the pins 53A and 53B inserted in the holes 9A and 9B and the holes 61A and 61B. In other words, the pin 53A and the pin 53B define a turn axis around which the jaw 21 is angularly movable about the shaft 5. The pins 53A and 53B may be fixed to the jaw 21 in the holes 61A and 61B. The pin 53A and the pin 53B are formed separately from each other, though they may be integrally formed with each other.

According to the present embodiment, the pin 53A is inserted in the hole 83A in the cover 31, and the pin 53B is inserted in the hole 83B in the cover 31, thereby keeping the cover 31 in engagement therewith. Furthermore, the pin 53A is inserted in the hole 61A in the jaw 21, and the pin 53B is inserted in the hole 61B in the jaw 21, thereby keeping the jaw 21 in engagement therewith. Therefore, the cover 31 is connected to the jaw 21 by the pins 53A and 53B. The cover 31 is thus prevented from coming off the jaw 21 as with the first embodiment. According to the present embodiment, the pins 53A and 53B act as pins that pass through the first holes, i.e., the holes 61A and 61B, defined in the jaw 21 and the second holes, i.e., the holes 83A and 83B, defined in the cover 31, and that are connected to the shaft 5.

Furthermore, the pin 53A is inserted in the hole 9A in the shaft 5 and the pin 53B is inserted in the hole 9B in the shaft 5, thereby connecting the jaw 21 and the shaft 5 to each other with the pins 53A and 53B. Therefore, the pins 53A and 53B keep the jaw 21 and the shaft 5 in engagement with each other and also keep the cover 31 and the jaw 21 in engagement with each other. In other words, the pins 53A and 53B that keep the shaft 5 and the jaw 21 in engagement with each other are used in common as engaging members that keep the cover 31 and the jaw 21 in engagement with each other. According to the present embodiment, therefore, a structure for maintaining the cover 31 and the jaw 21 in engagement with each other even if the cover 31 is deformed is realized without the need for an increase the number of parts used.

According to the present embodiment, the holes 83A and 83B in the cover 31 are larger than the holes 61A and 61B in the jaw 21. Furthermore, the holes 83A and 83B in the cover 31 are disposed coaxially with the holes 61A and 61B in the jaw 21. Therefore, the pins 53A and 53B in the holes 83A and 83B in the cover 31 are spaced from the edges of the holes 83A and 83B. Consequently, as with the first embodiment, when the jaw 21 is angularly moved with respect to the shaft 5, the edges of the holes 83A and 83B in the cover 31 are prevented from being pressed by the pins 53A and 53B.

The extensions 81A and 81B of the cover 31 may extend from the cover body 32 toward the proximal-end side and may be disposed between the protrusive members 24A and 24B in the groove 25. In this case, the hole 83A is disposed coaxially with the hole 61A inside of the protrusive member 24A, and the hole 83B is disposed coaxially with the hole 61B inside of the protrusive member 24B. The pin 53A is inserted in the hole 61A, the hole 83A, and the hole 9A, and the pin 53B is inserted in the hole 61B, the hole 83B, and the hole 9B, keeping the cover 31 and the jaw 21 in engagement with each other with the pins 53A and 53B and preventing the cover 31 from coming off the jaw 21.

The extensions 81A and 81B may be formed integrally with each other. In this case, the holes 83A and 83B are integrally defined therein, and a single pin passes through the holes 83A and 83B, the holes 61A and 61B, and the holes 9A and 9B, connecting the jaw 21, the cover 31, and the shaft 5 together with the pin.

According to the present embodiment, the pins 53A and 53B are fixedly disposed in the holes 61A and 61B in the jaw 21. However, the disclosed technology is not limited to such details. According to an embodiment, the pins 53A and 53B may not be fixedly disposed in the holes 61A and 61B in the jaw 21, but are fixedly disposed in the holes 9A and 9B in the shaft 5. In this case, the pins 53A and 53B are movable in the holes 61A and 61B with respect to the jaw 21. The holes 83A and 83B in the cover 31 are disposed coaxially with the holes 61A and 61B in the jaw 21. The inside diameters, i.e., cross-sectional areas, of the holes 83A and 83B are larger than the inside diameters, i.e., cross-sectional areas, of the holes 61A and 61B. Therefore, as the pins 53A and 53B abut against the edges of the holes 61A and 61B in the jaw 21 prior to the edges of the holes 83A and 83B in the cover 31, the pins 53A and 53B are preventing from pressing the edges of the holes 83A and 83B in the cover 31.

There may be employed a structure in which, when the handle 12 is operated, the movable shaft 18 may be moved with respect to the shaft 5 toward the proximal-end side, closing the second grip member 14 and the first grip member 13 toward each other, and the movable shaft 18 may be moved with respect to the shaft 5 toward the distal-end side, opening the second grip member 14 and the first grip member 13 away from each other. The joint structure between the cover 31 and the jaw 21 described hereinbefore is also applicable to such a structure.

Common Structure of the Embodiments

The treatment tool 1 includes the shaft 5 extending from the proximal-end side toward the distal-end side along the longitudinal axis C; the first jaw 13 disposed on the distal-end portion of the shaft 5; the second jaw 21 having the gripping surface 17 that faces the first jaw 13 and the back surface 26 that faces a side opposite the gripping surface 17, having the first hole 61A, 61B; 62A, 62B defined therein, and angularly movable about a turn axis 53A, 53B with respect to the shaft 5 so as to be opened or closed with respect to the first jaw 13; the movable shaft 18 movable along the longitudinal axis C with respect to the shaft 5 for angularly moving the second jaw 21 about the turn axis 53A, 53B with respect to the first jaw 13; the cover 31 disposed on the back surface 26 of the second jaw 21 and including the protrusion 37 that protrudes toward the proximal-end side with respect to the gripping surface 17 of the second jaw 21 and that has the second hole 38; 73A, 73B; 83A, 83B defined therein; and the pin 53A, 53B; 54 passing through the first hole 61A, 61B; 62A, 62B and the second hole 38; 73A, 73B; 83A, 83B and connected to the shaft 5 or the movable shaft 18.

The disclosed technology is not limited to the embodiments described hereinbefore, but various modifications may be made therein without departing from the scope of the invention when it is reduced to practice. The embodiments may be appropriately combined as much as possible, and the combinations offer combined advantages. Furthermore, the embodiments described hereinbefore include inventions in various stages, and various inventions can be extracted by appropriately combining a plurality of components that are disclosed.

In sum, the disclosed technology is directed to a treatment tool comprises an elongated shaft configured to extend from a proximal-end side toward a distal-end side along a longitudinal axis. A first jaw is disposed on the distal-end portion of the shaft. A second jaw having a gripping surface that faces the first jaw, an opposed back surface of the gripping surface and a first engaging portion. The second jaw is angularly movable about a turn axis of the first engaging portion so as to be opened or closed with respect to the first jaw. A movable shaft having a recess defined in a distal-end thereof and is movable along the longitudinal axis with respect to the shaft for angularly moving the second jaw about the turn axis with respect to the first jaw. A cover having a protrusion that protrudes toward a proximal-end side of the second jaw and a second engaging portion formed on the protrusion. The cover is disposed on the back surface of the second jaw in which the protrusion is disposed in the recess. The cover and the movable shaft being connected to one another by the second engaging portion and the second jaw and the movable shaft are connected to one another by the first engaging portion.

The first engaging portion includes a first hole defined in the second jaw. The second engaging portion includes a second hole defined in the protrusion. The treatment tool further comprises a pin inserted in the first hole and the second hole and being connected to the shaft or the movable shaft. In the treatment tool of claim 1, the cover is separated from the second jaw. In the treatment tool, the second jaw and the cover are spaced apart from another. An area of the second hole is larger than an area of the first hole. The pin is kept out of contact with an edge of the second hole even in a case where the movable shaft is moved along the longitudinal axis with respect to the shaft. The second jaw includes an arm portion protruding toward a proximal-end side with respect to the gripping surface and the first hole is defined in the arm portion. The second hole is spaced from the first hole in axial directions of the pin. In the treatment tool, the pin is connected to the shaft and defines the turn axis and the second jaw is mounted on the shaft by the pin. In the treatment tool, the second jaw includes an abutment member swingably mounted on the second jaw and the gripping surface is disposed on a surface of the abutment member that faces the first jaw.

While various embodiments of the disclosed technology have been described above, it should be understood that they have been presented by way of example only, and not of limitation. Likewise, the various diagrams may depict an example schematic or other configuration for the disclosed technology, which is done to aid in understanding the features and functionality that can be included in the disclosed technology. The disclosed technology is not restricted to the illustrated example schematic or configurations, but the desired features can be implemented using a variety of alternative illustrations and configurations. Indeed, it will be apparent to one of skill in the art how alternative functional, logical or physical locations and configurations can be implemented to implement the desired features of the technology disclosed herein.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent.

Additionally, the various embodiments set forth herein are described in terms of exemplary schematics, block diagrams, and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular configuration.

What is claimed is:

1. A treatment tool comprising:
    an elongated shaft configured to extend from a proximal-end side toward a distal-end side along a longitudinal axis;
    a first jaw disposed on the distal-end portion of the shaft;
    a second jaw having a gripping surface that faces the first jaw, an opposed back surface of the gripping surface and a first engaging portion, the first engaging portion including a first hole defined in the second jaw, the second jaw being angularly movable about a turn axis of the first engaging portion so as to be opened or closed with respect to the first jaw;
    a movable shaft having a recess defined in a distal-end thereof and being movable along the longitudinal axis with respect to the shaft for angularly moving the second jaw about the turn axis with respect to the first jaw;
    a cover having a protrusion that protrudes toward a proximal-end side of the second jaw and a second engaging portion formed on the protrusion, the second engaging portion including a second hole defined in the protrusion, the cover disposed on the back surface of the second jaw wherein
    the protrusion is disposed in the recess, and the cover and the movable shaft are connected to one another by the second engaging portion,
    the second jaw and the movable shaft are connected to one another by the first engaging portion, and
    an area of the second hole is larger than an area of the first hole.

2. The treatment tool of claim 1, further comprising a pin inserted in the first hole and the second hole, the pin being connected to the shaft or the movable shaft.

3. The treatment tool of claim 1, wherein
    the cover is separated from the second jaw.

4. The treatment tool of claim 1, wherein
    the second jaw and the cover are spaced apart from another.

5. The treatment tool of claim 2, wherein
    the pin is kept out of contact with an edge of the second hole
    when the movable shaft is moved along the longitudinal axis with respect to the shaft.

6. The treatment tool of claim 1, wherein
    the second jaw includes an arm portion protruding toward a proximal-end side with respect to the gripping surface; and
    the first hole is defined in the arm portion.

7. The treatment tool of claim 2, wherein
    the second hole is spaced from the first hole in axial directions of the pin.

8. The treatment tool of claim 2, wherein
    the pin is connected to the shaft and defines the turn axis; and
    the second jaw is mounted on the shaft by the pin.

9. The treatment tool of claim 1, wherein
the second jaw includes an abutment member swingably mounted on the second jaw; and
the gripping surface is disposed on a surface of the abutment member that faces the first jaw.

* * * * *